(12) United States Patent
Koch (10) Patent No.: US 6,990,979 B2
(45) Date of Patent: Jan. 31, 2006

(54) BREATHING EQUIPMENT WITH A CIRCUIT FOR BREATHING GAS

(75) Inventor: Jochim Koch, Ratzeburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 10/725,979

(22) Filed: Dec. 1, 2003

(65) Prior Publication Data

US 2004/0149288 A1 Aug. 5, 2004

(30) Foreign Application Priority Data

Feb. 4, 2003 (DE) ................. 103 04 394

(51) Int. Cl.
  A61M 15/00 (2006.01)
  A62B 19/00 (2006.01)
  A62B 7/00 (2006.01)
  A62B 23/02 (2006.01)

(52) U.S. Cl. .................... 128/204.13; 128/205.12; 128/205.13; 128/205.14; 128/205.15; 128/205.17; 128/205.22; 128/205.28

(58) Field of Classification Search .......... 128/205.12, 128/205.13, 205.14, 205.15, 205.17, 205.22, 128/205.28
See application file for complete search history.

(56) References Cited

U.S. PATENT DOCUMENTS

| | | | | |
|---|---|---|---|---|
| 1,808,177 A | * | 6/1931 | Putter | 128/205.28 |
| 1,983,475 A | * | 12/1934 | Lemoine | 128/202.26 |
| 3,815,592 A | * | 6/1974 | Staub, Jr. | 128/202.26 |
| 3,868,225 A | * | 2/1975 | Tidd | 422/122 |
| 3,923,057 A | * | 12/1975 | Chalon | 128/203.16 |
| 4,154,236 A | * | 5/1979 | Eckstein et al. | 128/202.26 |
| 4,164,218 A | * | 8/1979 | Martin | 128/201.18 |
| 4,188,947 A | * | 2/1980 | Pasternack | 128/202.26 |
| 4,232,667 A | * | 11/1980 | Chalon et al. | 128/203.26 |
| 4,314,566 A | * | 2/1982 | Kiwak | 128/204.15 |
| 4,334,533 A | * | 6/1982 | Henkin | 128/205.28 |
| 4,350,662 A | * | 9/1982 | Dowgul et al. | 422/122 |
| 4,491,130 A | * | 1/1985 | Pasternack | 128/202.26 |
| 4,515,156 A | * | 5/1985 | Khudosovtsev et al. | 128/202.26 |
| 4,635,629 A | | 1/1987 | Thorp et al. | |
| 5,038,768 A | * | 8/1991 | McGoff et al. | 128/202.26 |
| 5,038,792 A | * | 8/1991 | Mault | 600/531 |
| 5,044,363 A | * | 9/1991 | Burkhart | 128/205.27 |
| 5,269,293 A | * | 12/1993 | Loser et al. | 128/204.15 |
| 5,487,380 A | * | 1/1996 | Grabenkort | 128/204.15 |

(Continued)

FOREIGN PATENT DOCUMENTS

DE 879 651 6/1953

(Continued)

OTHER PUBLICATIONS

Conzen, Peter F.; Degradation of Inhalation Anaesthetics by CO2 Absorbers May 29, 1999; European Society of Anaesthesiologists.*

Primary Examiner—Henry Bennett
Assistant Examiner—Nihir Patel
(74) Attorney, Agent, or Firm—McGlew & Tuttle PC (57) ABSTRACT

Breathing equipment with a circuit for breathing gas and with a flat calcium hydroxide absorber (1) is cooled by an evaporating agent with improved cooling. A gas volume flow of at least 60 L per minute is admitted to the outer surface (14) of the calcium hydroxide absorber (1) receiving the evaporating agent by at least one gas delivery device (5). The evaporating agent is delivered to the outer surface (14) of the calcium hydroxide absorber (1) by an admitted pressure from an evaporating agent reservoir (10) via at least one connection line (12).

37 Claims, 6 Drawing Sheets

U.S. PATENT DOCUMENTS

| | | | |
|---|---|---|---|
| 5,613,488 A * | 3/1997 | Schwichtenberg et al. | 128/202.26 |
| 5,706,799 A * | 1/1998 | Imai et al. | 128/205.12 |
| 5,722,393 A * | 3/1998 | Bartel et al. | 128/204.15 |
| 6,128,963 A * | 10/2000 | Bromster | 73/861.52 |
| 6,279,576 B1 * | 8/2001 | Lambert | 128/205.28 |
| 6,634,355 B2 * | 10/2003 | Colas | 128/203.12 |
| 6,684,881 B2 * | 2/2004 | Fr.ang.nberg | 128/202.26 |

FOREIGN PATENT DOCUMENTS

| | | |
|---|---|---|
| DE | 879 651 B | 6/1953 |
| DE | 916 384 | 8/1954 |
| DE | 916 384 B | 8/1954 |
| DE | 694 29 817 | 10/1994 |
| DE | 694 29 817 T2 | 8/2002 |
| GB | 488666 | 7/1938 |

\* cited by examiner

BREATHING EQUIPMENT WITH A CIRCUIT FOR BREATHING GAS

FIELD OF THE INVENTION

The present invention pertains to a respirator with a circuit for breathing gas with a flat calcium hydroxide absorber cooled by an evaporating agent.

BACKGROUND OF THE INVENTION

Respiration is performed in a circuit in breathing equipment, especially in gas masks, to reduce the weight and to prolong the service life, and only the amount of oxygen having been consumed is added from a pressurized gas reserve. To prevent the carbon dioxide ($CO_2$) breathed out from accumulating in the circuit to nonphysiological levels, an absorber with an absorbent, which removes the $CO_2$ from the breathing circuit, is present in the circuit. Prior-art absorbents consist of one or more alkali hydroxides and contain or consist especially of calcium hydroxide. Heat and moisture are generated during the chemical reaction taking place between the $CO_2$ and the absorbent, and this may lead to an increase in the breathing gas temperature and to discomfort for the person respirated through the breathing equipment. Thus, temperatures that were up to 15° C. higher than the particular ambient temperature were measured after the absorber, and the breathing gas is saturated with moisture. It was therefore proposed that gas masks that are used for a prolonged period of time of several hours be equipped with a breathing gas cooler.

The use of paraffin or a salt as a coolant for such breathing equipment is disclosed in DE 879 651 B; the evaporation temperature or the melting point is between 40° C. and 180° C. here, and the alkali cartridge is surrounded by the coolant.

As an addition to DE 879 651 B, DE 916 384 B shows as a characterizing feature that the cooling jacket is formed from at least one layer of corrugated board provided especially with continuous longitudinal openings, which are covered by smooth board layers on both sides, so that channels are formed, which facilitate the absorption of cooling liquid by the jacket.

SUMMARY OF THE INVENTION

The object of the present invention is to provide breathing equipment with a circuit for breathing gas with improved cooling for the breathing gas.

According to the invention, breathing equipment is provided with a circuit for breathing gas and with a flat calcium hydroxide absorber cooled by an evaporating agent. The equipment admits a gas volume flow of at least 60 L per minute to the outer surface of the calcium hydroxide absorber receiving the evaporating agent. The evaporating agent is delivered to the outer surface of the calcium hydroxide absorber by means of admitted pressure from a evaporating agent reservoir via at least one connection line.

An essential advantage of the present invention is the flat design of the especially parallelepipedic calcium hydroxide absorber with a depth of up to 70 mm, on average, so that the heat conduction paths from the calcium hydroxide pellets with poor thermal conductivity to the outer surface of the calcium hydroxide absorber is as short as possible. This is absolutely necessary because the heat output to be removed during the absorption of $CO_2$ in the calcium hydroxide is not transferred efficiently to the outer surface of the calcium hydroxide absorber: In the case of a hypothetical period of use of four hours and a respiratory minute volume of 30 L per minute of the user of the breathing equipment, a thermal energy of about 750 kJ is generated in about 3 L of calcium hydroxide, and this amount of thermal energy must be removed according to the present invention in order to achieve the cooling of the calcium hydroxide absorber.

Instead of a flat, parallelepipedic calcium hydroxide absorber, it is also possible to use a plurality of absorbers arranged in parallel in a gas flow connection or absorbers provided with at least one continuous ventilation slot. It is essential that the calcium hydroxide in the calcium hydroxide absorber have the shortest possible heat conduction paths to the outer surface of the absorber.

A hydrophilic material, which is moistened with the evaporating agent and makes possible good evaporation and cooling associated therewith, is applied or clamped on the outer surface of the calcium hydroxide absorber. At the same time, this hydrophilic material has the best heat conduction possible so that no additional thermal resistance will build up for the heat conduction from the calcium hydroxide. Cotton and silk have proved to be especially suitable materials for the outer surface of the calcium hydroxide absorber for absorbing the evaporating agent.

The use of a gas delivery means with a gas volume flow of at least 60 L per minute proved to be absolutely necessary in order to generate the amounts of convection air necessary for the heat transport from the calcium hydroxide absorber. An electrically driven positive displacement blower designed as a fan is used in the simplest case, which delivers a gas volume flow of preferably 150 L to 250 L per minute as uniformly as possible along the entire outer surface of the calcium hydroxide absorber in order to achieve the evaporation of the evaporating agent, especially water, an aqueous solution or a mixture with water, which cools the environment, as well as to make possible the convective cooling, both of which are necessary to remove the thermal energy generated in the calcium hydroxide absorber containing, e.g., 3 L of calcium hydroxide.

Corresponding measurements confirmed these results when the user of the breathing equipment generates a usual respiratory minute volume of 30 L per minute and a corresponding amount of $CO_2$, which is reacted in the calcium hydroxide absorber with an associated release of thermal energy.

The evaporating agent is distributed on the outer surface as uniformly as possible for the good evaporation of the evaporating agent over the entire outer surface of the calcium hydroxide absorber. The evaporating agent reservoir is provided for this purpose with a hose type distributor in order to distribute the evaporating agent, e.g., on all four sides of a parallelepipedic calcium hydroxide absorber by means of the corresponding connection lines.

Each of the outlets of the connection lines ending on the outer surface of the calcium hydroxide absorber is preferably provided with a porous or fibrous material such as cellulose acetate, so that an equal pressure resistance and the most uniform moistening possible of the outer surface of the calcium hydroxide absorber are guaranteed.

It is necessary according to the present invention to admit pressure to the evaporating agent in the connection lines for the uniform distribution of the evaporating agent on the outer surface of the calcium hydroxide absorber. Pressure is admitted for this purpose, in particular, to the evaporating agent reservoir by means of a pretensioned spring, or pressure is generated in the connection lines by means of an electrically or mechanically driven pump, especially by means of a hose pump. If the breathing equipment has a breathing bag, which is in gas flow connection with the circulation and can be reversibly inflated by the respiratory flow, the breathing bag is connected to the pump either purely mechanically or electromechanically in a variant of the present invention such that the movement of the breathing bag is utilized as the drive for the pump. For example, a slight rotation of a hose pump may thus occur during each expansion or resetting of the breathing bag via a lever and locking teeth or a roller clutch. The evaporating surface corresponding to the outer surface of the calcium hydroxide absorber is then flooded in proportion to the breathing stroke and the respiration rate. The pump is switched on automatically at the start of the breathing equipment and stops automatically when the user of the breathing equipment detaches his breathing tubes from the breathing equipment. Continued pumping and the running out of the evaporating agent are thus prevented from occurring.

Besides a pump or spring mechanism alternate means may be used to admit pressure to the evaporating agent in the connection lines for the uniform distribution of the evaporating agent on the outer surface of the calcium hydroxide absorber. One advantageous approach is to exert pressure on the evaporating agent reservoir. This may be done by providing a pressurized gas contained in a separate gas reservoir or by preferably using the breathing gas pressure of the breathing gas reservoir which is a standard component of most breathing equipment used for personal protection in mining operations, fire rescue devices and similar devices.

The use of pressurized fluid to exert pressure on the evaporating agent may be by use of a vessel, tank, cartridge or other structure such as a movable pump piston for the separation of media, pressure applying fluid and the liquid evaporation agent, as well as providing pressure transmission between the media. The separation and pressure transmission feature may be provided via a flexible tank within a vessel, tank, cartridge or other structure or via a flexible membrane, diaphragm, bellows or bubble structure within a vessel, tank, cartridge or other structure.

An exemplary embodiment of the present invention will be explained below by means of the schematic figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
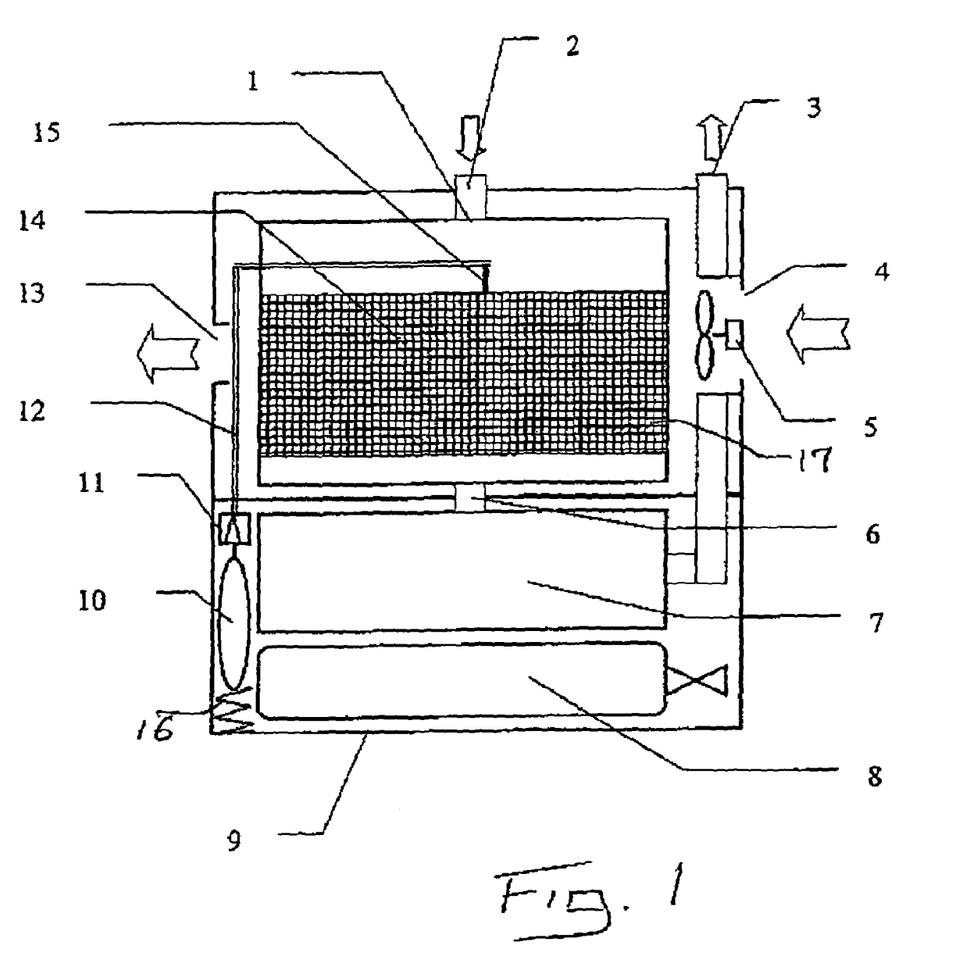
FIG. 1 is a partially schematic sectional view through a breathing device or the breathing equipment showing the most important components according to a first embodiment of the invention showing two alternative evaporating agent delivery means.
Figure 2:
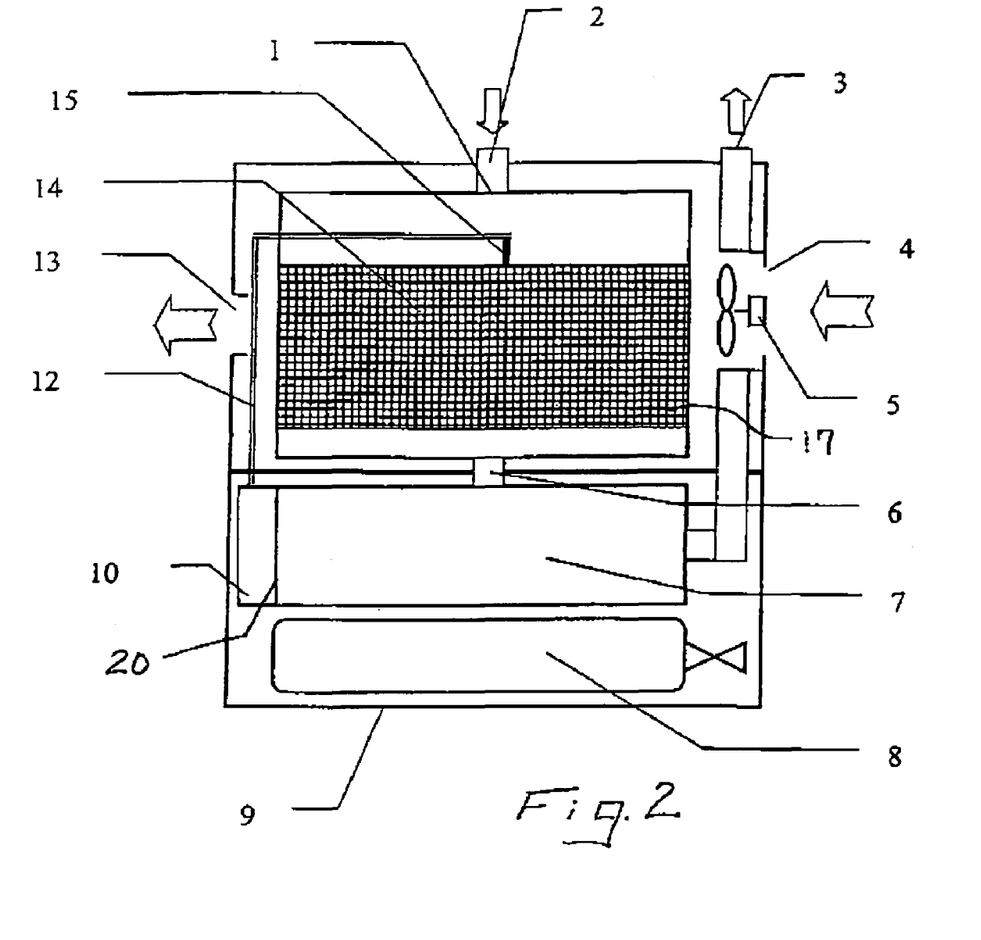
FIG. 2 is a partially schematic sectional view through a breathing device or the breathing equipment showing the most important components according to a second embodiment of the invention.
Figure 3:
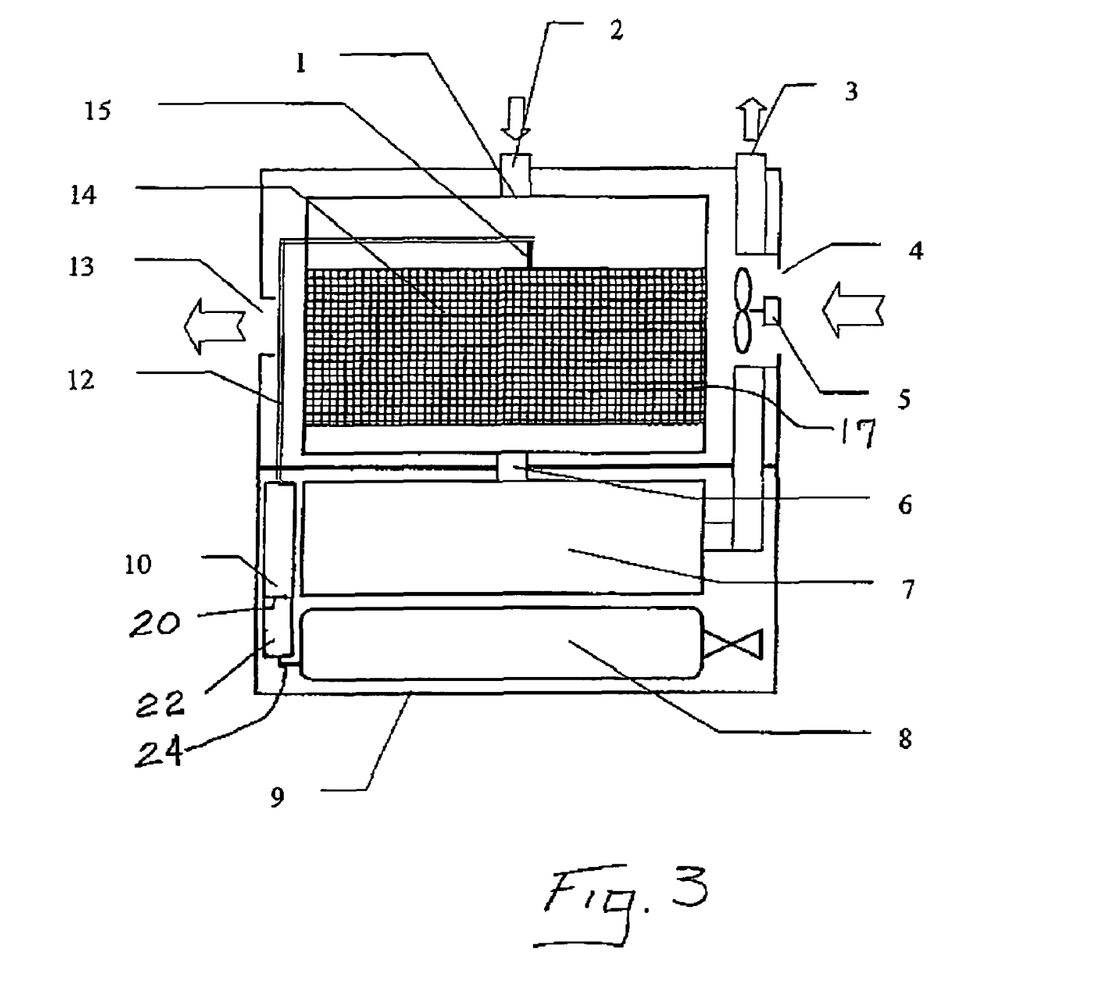
FIG. 3 is a partially schematic sectional view through a breathing device or the breathing equipment showing the most important components according to a third embodiment of the invention.

Referring to the drawings in particular, FIGS. 1, 2 and 3 show three embodiments of breathing equipment with a circuit for breathing gas according to the invention. In each of these embodiments a calcium hydroxide absorber 1 is located in a breathing device housing or breathing equipment housing 9. The expired air of the user of the breathing equipment is released via tubes and the inlet 2 into the calcium hydroxide absorber 1. The user of the breathing equipment again breathes from the breathing equipment via tubes via the outlet 3. The user breathes in directly from the breathing bag 7, which is connected to the calcium hydroxide absorber 1 via a gas connection line 6. The circuit for breathing gas is now closed. A first opening 4 in the breathing equipment housing 9 is arranged in each exemplary embodiment on the side, i.e., on the right in each figure, on which side an electrically driven fan is also arranged as a gas delivery means 5, which draws in air from the environment. The air is removed on the opposite side through the second opening 13 shown on the left in the figure in the direction of the arrow. The air now sweeps over the outer surface 14 of the calcium hydroxide absorber 1 and removes the evaporated evaporating agent, especially water, with the air being delivered into the environment.

The outer surface 14 of the calcium hydroxide absorber 1 is covered with a hydrophilic web of fabric 17, e.g., one made of cotton, which is uniformly wetted and moistened with evaporating agent from the evaporating agent reservoir 10 via the at least one connection line outlet 15 of the at least one connection line 12.

According to the embodiment of FIG. 1, the supply with evaporating agent 30 is ensured by an evaporating agent delivery means in the form of a pump 11, which is driven either mechanically or electrically and is designed especially as a hose pump. In a variant of the embodiment of FIG. 1 of the present invention, the evaporating agent delivery means comprises a pretensioned spring 16 acting on a flexible portion of the evaporating agent reservoir 10.

According to each of the embodiments the evaporating agent reservoir 10 is dimensioned such that it contains a sufficient amount of evaporating agent for the duration of the mission of the user of the breathing equipment or of the breathing equipment. In the case of water, 300 mL to 400 mL are sufficient for a service life of 4 hours. A high-pressure oxygen cylinder 8 with a pressure regulator may be provided to continuously replenish the oxygen consumed in the circulation. The cylinder 8 is located in the breathing equipment housing 9.

In another variant of the embodiment of FIG. 1 of the present invention, the pump 11 is connected to the breathing bag 7 via a mechanical or electromechanical connection in order to adapt the cooling and consequently the amount of evaporating agent released from the evaporating agent reservoir 10 to the respiratory minute volume of the user of the breathing equipment, to start and also to end the evaporative cooling by the delivery of the evaporating agent to the outer surface 14.

The embodiment of FIG. 2 is similar to the embodiment of FIG. 1 except the evaporating agent delivery means is a media separation and pressure transmission means or device 20, employed to supply the evaporating agent. The media separation and pressure transmission device 20 uses high pressure fluid as the source of pressure to supply the evaporating agent. Various embodiments of media separation and pressure transmission device 20 are described below with reference to FIGS. 4A to 6C. In the embodiment of FIG. 2, the breathing bag 7 is the source of the high pressure fluid acting to apply pressure on the evaporating agent via the media separation and pressure transmission device 20.

The embodiment of FIG. 3 is similar to the embodiment of FIG. 1 except the a media separation and pressure transmission device 20 is employed to supply the evaporating agent. The media separation and pressure transmission device 20 uses high pressure fluid as the source of pressure to supply the evaporating agent. Various embodiments of media separation and pressure transmission device 20 are described below with reference to FIGS. 4A to 6C. In the embodiment of FIG. 3, pressurized gas contained in a separate reservoir 22 is the source of the high pressure fluid acting to apply pressure on the evaporating agent via the media separation and pressure transmission device 20. The separate reservoir 22 may alternatively be connected to the high-pressure oxygen cylinder 8 via a connection line 24 or instead of a separate reservoir 22 or reservoir 22 acting as an intermediary, the high-pressure oxygen cylinder 8 may be the source of the high pressure fluid acting to apply pressure on the evaporating agent via the media separation and pressure transmission device 20.

Figure 4A:
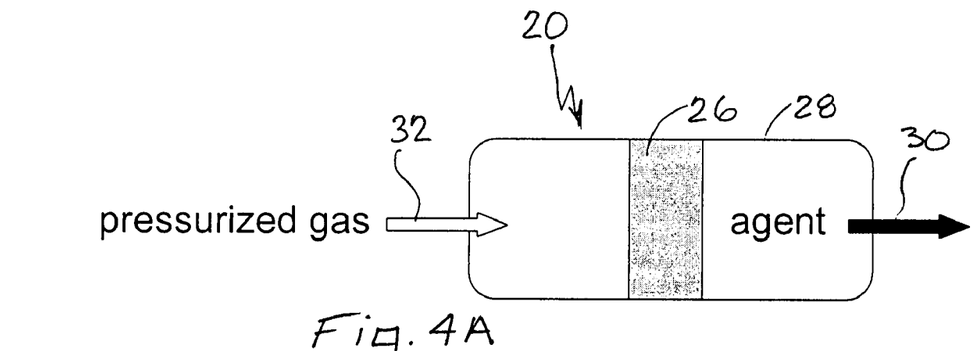
FIG. 4A is a schematic view showing a media separation and pressure transmission device having a piston.

FIG. 4A schematically shows the media separation and pressure transmission device 20 having a piston 26 movable in a tank 28. The tank 28 is in fluid communication with the agent 30 and the high pressure fluid or pressurized gas 32. By admitting the pressurized gas 32 into the tank 28, a force is applied on the piston 26 (that is higher than the force applied on the other side of the piston by the evaporating agent) resulting in the supply of evaporating agent 30 to the outer surface 14 of the calcium hydroxide absorber 1.

Figures 4B, 4C:
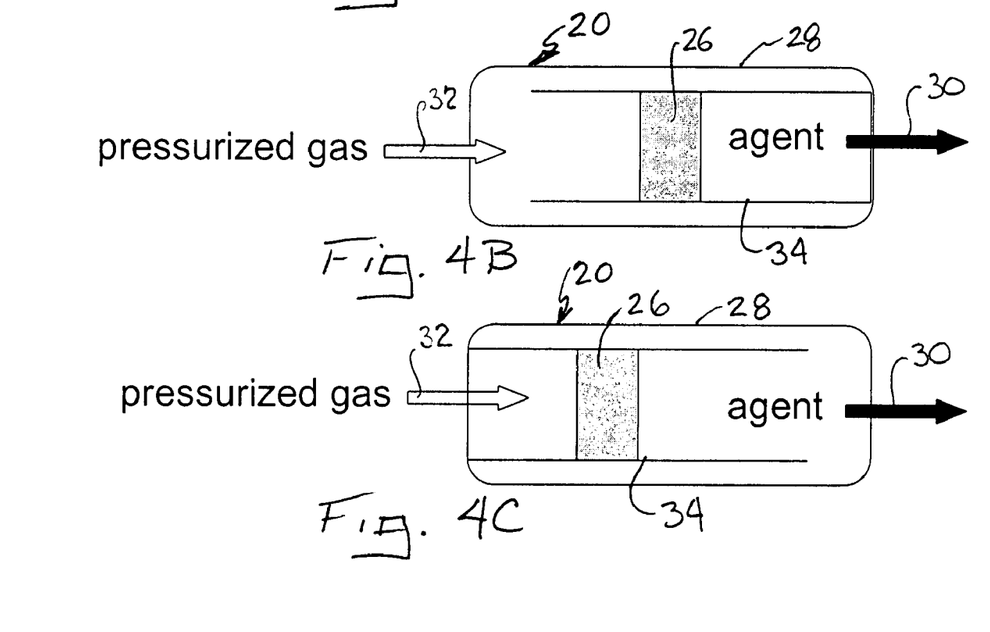
FIG. 4B is a schematic view showing another media separation and pressure transmission device having a piston.
FIG. 4C is a schematic view showing another media separation and pressure transmission device having a piston.

FIG. 4B schematically shows the media separation and pressure transmission device 20 having a piston 26 movable in a cartridge 34 that is in a tank 28. The cartridge 34 is in fluid communication with the agent 30 on one side of the piston 26. The other side of the piston 26 is in fluid communication with the high pressure fluid or pressurized gas 32 in the interior of the tank 28. By admitting the pressurized gas 32 into the tank 28, a force is applied on the piston 26 resulting in the supply of evaporating agent 30 to the outer surface 14 of the calcium hydroxide absorber 1.

FIG. 4C schematically shows the media separation and pressure transmission device 20 having a piston 26 movable in a cartridge 34 that is in a tank 28. The cartridge 34 is in fluid communication with the high pressure fluid or pressurized gas 32 on one side of the piston 26. The other side of the piston 26 is in fluid communication with the agent 30 in the interior of the tank 28. By admitting the pressurized gas 32 into the cartridge 34, a force is applied on the piston 26 resulting in the supply of evaporating agent 30 to the outer surface 14 of the calcium hydroxide absorber 1.

Figure 5A:
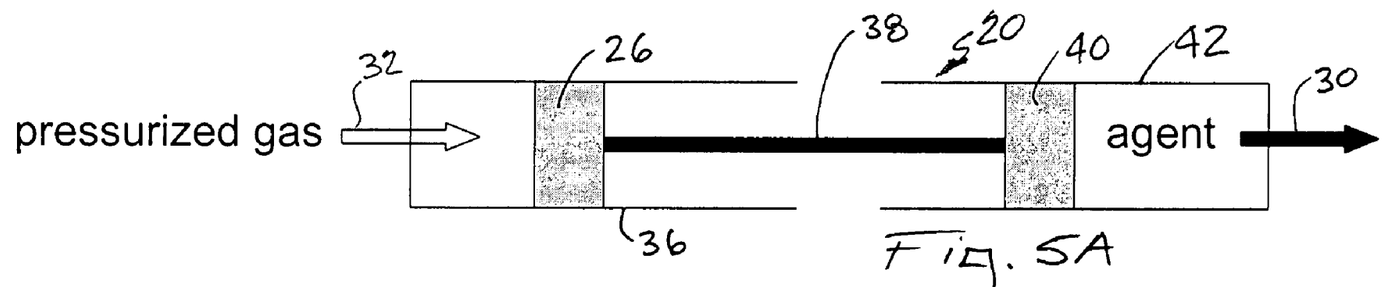
FIG. 5A is a schematic view showing a media separation and pressure transmission device having plural pistons and cylinders.

FIG. 5A schematically shows the media separation and pressure transmission device 20 having a first piston 26 and a cylinder 36 cooperating with a second piston 40 in a cylinder 42 via a connection element 38. The cylinder 36 is in fluid communication with the high pressure fluid or pressurized gas 32 on a pressure side of the piston 26. The other piston 40 is in fluid communication with the agent 30 in the interior of the cylinder 42. By admitting the pressurized gas 32 into the cartridge 34, a force is applied on the piston 26 and transmitted to piston 40 via connecting element 38, resulting in the supply of evaporating agent 30 to the outer surface 14 of the calcium hydroxide absorber 1.

Figure 5B:
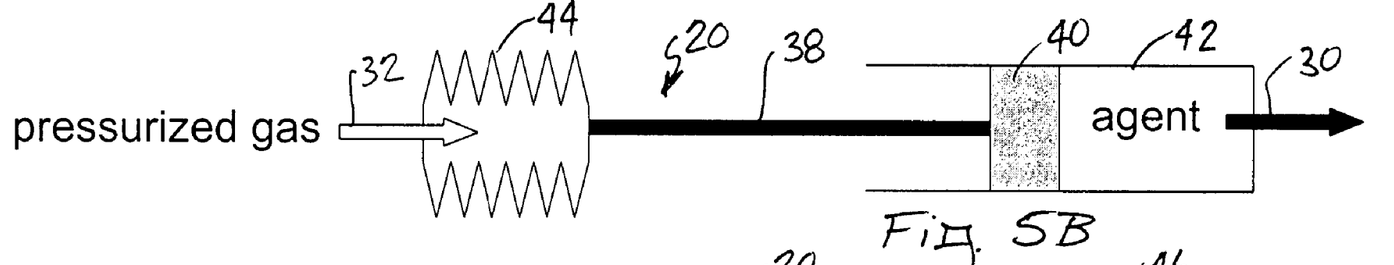
FIG. 5B is a schematic view showing a media separation and pressure transmission device having a bellows arrangement for the high pressure fluid and with a piston and cylinder for the evaporating agent.

FIG. 5B schematically shows the media separation and pressure transmission device 20 having a bellows 44 cooperating with a piston 40 in a cylinder 42 via a connection element 38. The bellows 44 is in fluid communication with the high pressure fluid or pressurized gas 32. The piston 40 is in fluid communication with the agent 30 in the interior of the cylinder 42. By admitting the pressurized gas 32 into the bellows 44, a force is applied to expand the bellows 44 and the expansion force acts on piston 40 via connecting element 38, resulting in the supply of evaporating agent 30 to the outer surface 14 of the calcium hydroxide absorber 1.

Figure 5C:
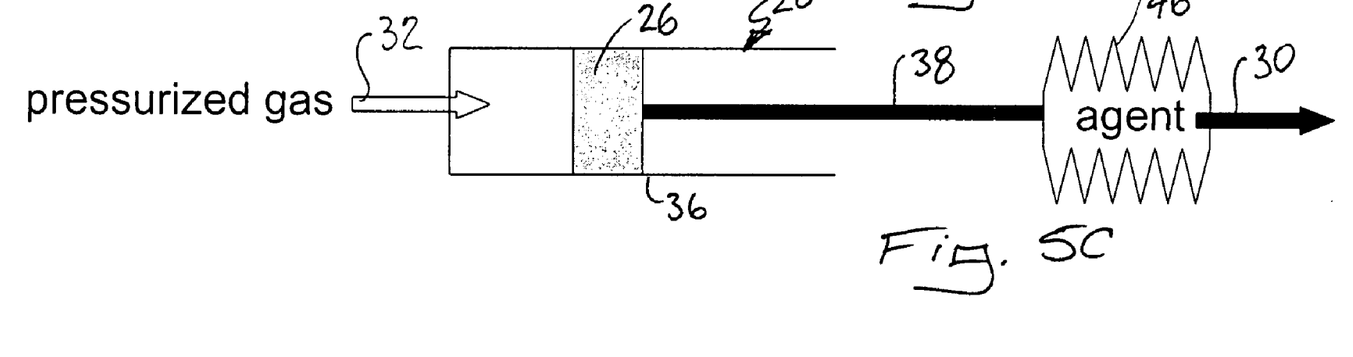
FIG. 5C is a schematic view showing a media separation and pressure transmission device having a bellows arrangement for the evaporating agent with a piston and cylinder for the high pressure fluid.

FIG. 5C schematically shows the media separation and pressure transmission device 20 having a piston 26 and a cylinder 36 cooperating with a bellows 46 via a connection element 38. The cylinder 36 is in fluid communication with the high pressure fluid or pressurized gas 32 on a pressure side of the piston 26. The bellows 46 is in fluid communication with the agent 30 in the interior of the bellows 46. By admitting the pressurized gas 32 into the bellows 44, a force is applied to the piston 26, which acts on piston bellows 46 via connecting element 38 to contract the bellows 46 resulting in the supply of evaporating agent 30 to the outer surface 14 of the calcium hydroxide absorber 1.

Figure 6A:
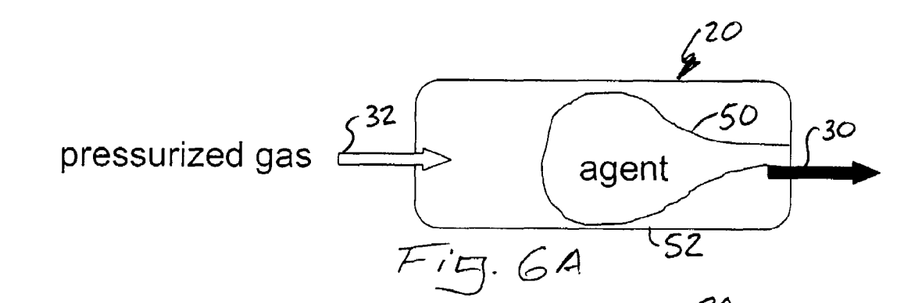
FIG. 6A is a schematic view showing a media separation and pressure transmission device having a flexible agent reservoir or bellows in a pressure tank.

FIG. 6A schematically shows the media separation and pressure transmission device 20 having a flexible agent reservoir or bellows (or bubble membrane) 50 in a pressure tank 52. By admitting the pressurized gas 32 into the tank 52, a force acts on bellows 50 to contract the bellows 50 resulting in the supply of evaporating agent 30 to the outer surface 14 of the calcium hydroxide absorber 1.

Figure 6B:
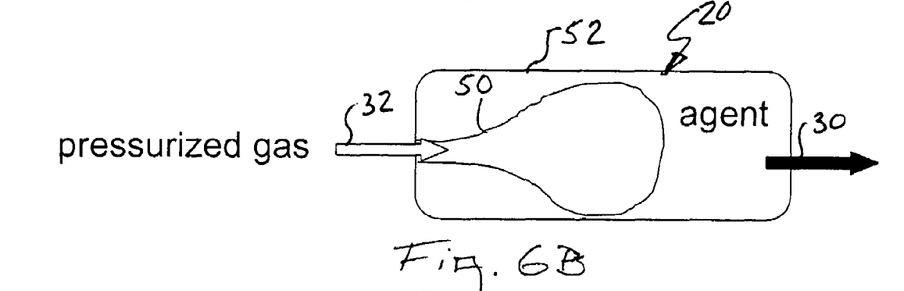
FIG. 6B is a schematic view showing a media separation and pressure transmission device having a flexible bubble or bellows receiving the high pressure fluid with the evaporation agent in the tank.

FIG. 6B schematically shows the media separation and pressure transmission device 20 having a flexible agent reservoir or bellows (or bubble membrane) 50 in a pressure tank 52. By admitting the pressurized gas 32 into the bellows 50, a force acts on bellows 50 to expand the bellows 50 resulting in the supply of evaporating agent 30 to the outer surface 14 of the calcium hydroxide absorber 1.

Figure 6C:
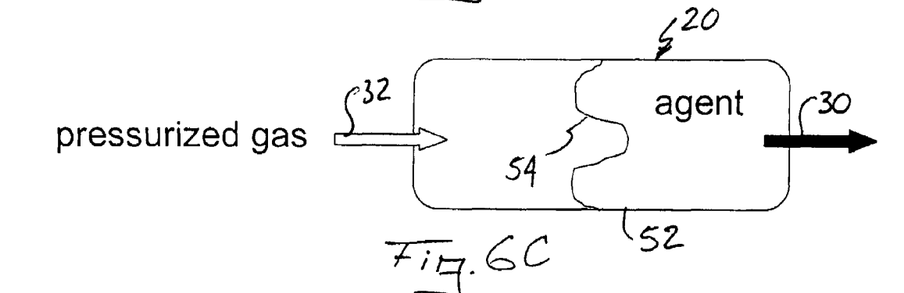
FIG. 6C is a schematic view showing a media separation and pressure transmission device with a flexible membrane or bellows in the pressure tank and the high pressure fluid on one side and with the evaporation agent on the other side.

FIG. 6C schematically shows the media separation and pressure transmission device 20 having a diaphragm membrane 54 in a pressure tank 52. By admitting the pressurized gas 32 into the tank 52, a force acts on diaphragm membrane 54 resulting in the supply of evaporating agent 30 to the outer surface 14 of the calcium hydroxide absorber 1.

While specific embodiments of the invention have been shown and described in detail to illustrate the application of the principles of the invention, it will be understood that the invention may be embodied otherwise without departing from such principles.

What is claimed is:

1. A breathing device, comprising:
   a breathing gas circuit with a connected calcium hydroxide absorber for flow of breathing gas through said calcium hydroxide absorber;
   means for generating a gas volume flow of at least 60 L per minute separate from the flow of breathing gas with the gas flow being admitted to an outer surface of the calcium hydroxide absorber; and
   an evaporating agent delivery means for delivering a liquid evaporating agent to the outer surface of the calcium hydroxide absorber, by admitted pressure, from an evaporating agent reservoir containing the liquid evaporating agent via at least one connection line whereby the outer surface receives the liquid evaporation agent and is cooled by said gas flow and said evaporating agent.

2. A breathing device in accordance with claim 1, wherein the outer surface of the calcium hydroxide absorber receiving the evaporating agent is provided with a hydrophilic fabric or nonwoven.

3. A breathing device in accordance with claim 1, wherein a gas volume flow of 150 L to 250 L per minute is admitted to the outer surface of said calcium hydroxide absorber by said means for generating a gas volume flow.

4. A breathing device in accordance with claim 1, wherein the gas delivery means is a positive displacement blower driven electrically or by compressed gas.

5. A breathing device in accordance with claim 1, wherein the breathing device is a gas mask or part of a gas mask system or a part of an anesthesia apparatus.

6. A breathing device in accordance with claim 1, wherein said evaporating agent delivery means includes an electrically or mechanically driven pump.

7. A breathing device in accordance with claim 1, wherein said evaporating agent delivery means comprises a pretensioned spring and said evaporating agent reservoir is provided with said pretensioned spring, so that the evaporating agent is delivered to the outer surface of the calcium hydroxide absorber by means of an admitted pressure.

8. A breathing device in accordance with claim 1, wherein the evaporating agent is water, a solution containing water or a mixture containing water.

9. A breathing device in accordance with claim 1, wherein the at least one said connection line between said evaporating agent reservoir and the outer surface of the calcium hydroxide absorber is provided with a porous or fibrous material.

10. A breathing device in accordance with claim 1, further comprising: a breathing bag, which can be inflated by the breathing gas, in gas flow connection with said breathing gas circuit, said breathing bag being mechanically or electromechanically connected with a pump of said evaporating agent delivery means, so that said pump is actuated as a function of respiratory activity and movement of the breathing bag.

11. A breathing device in accordance with claim 1, wherein said evaporating agent delivery means includes a media separation and pressure transmission means separating a high pressure fluid as a source of pressure from the evaporating agent to apply pressure on the evaporating agent to supply the evaporating agent.

12. A breathing device in accordance with claim 11, further comprising: a breathing bag, which can be inflated by the breathing gas, in gas flow connection with said breathing gas circuit wherein said high pressure fluid of said media separation and pressure transmission means is gas in said breathing bag.

13. A breathing device in accordance with claim 11, further comprising: a pressurized gas reservoir, wherein said high pressure fluid of said media separation and pressure transmission means is gas in said pressurized gas reservoir.

14. A breathing device in accordance with claim 13, wherein said pressurized gas reservoir is a high-pressure oxygen cylinder in regulated gas flow connection with said breathing gas circuit.

15. A breathing device in accordance with claim 11, wherein said media separation and pressure transmission means includes a piston and tank with said piston separating said high pressure fluid from said evaporating agent to apply pressure on the evaporating agent to supply the evaporating agent.

16. A breathing device in accordance with claim 11, wherein said media separation and pressure transmission means includes a high pressure fluid arrangement with a piston and cylinder or a bellows in fluid communication with said high pressure fluid and an evaporating agent fluid arrangement with a piston and cylinder or a bellows in fluid communication with said evaporating agent and further comprises a connecting element connecting said high pressure fluid arrangement with said evaporating agent fluid arrangement to apply pressure on the evaporating agent to supply the evaporating agent.

17. A breathing device in accordance with claim 11, wherein said media separation and pressure transmission means includes a tank with said membrane separating said high pressure fluid from said evaporating agent to apply pressure on the evaporating agent to supply the evaporating agent.

18. A breathing device in accordance with claim 1, wherein said calcium hydroxide absorber has the form of one or more parallelepipedic containers and of a container with an elliptical base, which are in gas flow connection.

19. A breathing device in accordance with claim 2, wherein said hydrophilic fabric or nonwoven is made of cotton or silk.

20. A breathing device in accordance with claim 1, wherein said evaporating agent delivery means includes a hose pump.

21. A breathing device in accordance with claim 1, wherein the at least one said connection line between said evaporating agent reservoir and the outer surface of the calcium hydroxide absorber is provided with cellulose acetate.

22. A breathing device, comprising:
   a device housing with an absorber space connected to a cooling flow passage;
   calcium hydroxide absorber disposed in said absorber space and having an outer surface;
   a breathing gas circuit connected to said calcium hydroxide absorber for flow of breathing gas through said calcium hydroxide absorber;
   an evaporating agent reservoir;
   an evaporating agent disposed in said reservoir in a liquid state;
   a connection line;
   an evaporating agent delivery device, delivering said evaporating agent in a liquid state to the outer surface of the calcium hydroxide absorber by admitted pressure from said evaporating again reservoir via said connection line; and a flow generator, generating a cooling gas volume flow of at least 60 L per minute that is separate from said flow of breathing gas and is directed to an outer surface of the calcium hydroxide absorber via said cooling flow passage to evaporate said evaporating agent delivered to said outer surface.

23. A breathing device in accordance with claim 22, further comprising a hydrophilic fabric or nonwoven provided at said outer surface of the calcium hydroxide absorber for receiving said evaporating agent via said connection line.

24. A breathing device in accordance with claim 22, wherein said flow generator is a positive displacement blower driven electrically or by compressed gas.

25. A breathing device in accordance with claim 22, wherein said evaporating agent delivery device comprises a pretensioned spring, said evaporating agent reservoir being provided with said pretensioned spring, so that the evaporating agent is delivered to the outer surface of the calcium hydroxide absorber by means of an admitted pressure.

26. A breathing device in accordance with claim 22, wherein the evaporating agent is water, a solution containing water or a mixture containing water and said connection line between said evaporating agent reservoir and the outer surface of the calcium hydroxide absorber is provided with a porous or fibrous material.

27. A breathing device in accordance with claim 22, further comprising: a breathing bag, which can be inflated by the breathing gas, in gas flow connection with said breathing gas circuit, said breathing bag being mechanically or electromechanically connected with a pump of said flow, generator, whereby said pump is actuated as a function of respiratory activity and movement of the breathing bag.

28. A breathing device in accordance with claim 22, wherein said evaporating agent delivery device includes a media separation and pressure transmission device separating a high pressure fluid as a source of pressure from the evaporating agent to apply pressure on the evaporating agent to supply the evaporating agent.

29. A breathing device in accordance with claim 28, further comprising: a breathing bag, which can be inflated by the breathing gas, in gas flow connection with said breathing gas circuit wherein said high pressure fluid of said media separation and pressure transmission device is gas in said breathing bag.

30. A breathing device in accordance with claim 28, further comprising: a pressurized gas reservoir, wherein said high pressure fluid of said media separation and pressure transmission device is gas in said pressurized gas reservoir.

31. A breathing device in accordance with claim 30, wherein said pressurized gas reservoir is a high-pressure oxygen cylinder in gas flow connection with said breathing gas circuit.

32. A breathing device in accordance with claim 28, wherein said media separation and pressure transmission device includes a piston and tank with said piston separating said high pressure fluid from said evaporating agent to apply pressure on the evaporating agent to supply the evaporating agent.

33. A breathing device in accordance with claim 32, wherein said media separation and pressure transmission device includes a high pressure fluid arrangement with a piston and cylinder or a bellows in fluid communication with said high pressure fluid and an evaporating agent fluid arrangement with a piston and cylinder or a bellows in fluid communication with said evaporating agent and further comprises a connecting element connecting said high pressure fluid arrangement with said evaporating agent fluid arrangement to apply pressure on the evaporating agent to supply the evaporating agent.

34. A breathing device in accordance with claim 28, wherein said media separation and pressure transmission device includes a tank with a membrane separating said high pressure fluid from said evaporating agent to apply pressure on the evaporating agent to supply the evaporating agent.

35. A breathing device in accordance with claim 1, wherein said calcium hydroxide absorber is parallelepipedic having a thickness dimension that is less than a height dimension and less than a width dimension to provide a substantially flat profile.

36. A breathing device in accordance wish claim 28, wherein said calcium hydroxide absorber is parallelepipedic having a thickness dimension that is less than a height dimension and less than a width dimension to provide a substantially flat profile.

37. A breathing device, comprising:
a device housing with an absorber space connected to a cooling flow passage;
an absorber in said absorber space, said absorber having an outer surface and having an absorbent for removing $CO_2$ from breathing gas;
a breathing gas circuit connected to said absorber for the passage of breathing gas through said absorber, wherein heat is generated during a chemical reaction taking place between the $CO_2$ in the breathing gas and the absorbent;
a liquid reservoir;
a liquid in said reservoir;
liquid delivery means for delivering said liquid from said reservoir to said outer surface; and
a gas flow generator for generating a gas volume flow directed to said outer surface and separate from said breathing gas to evaporate the liquid delivered to said outer surface for removing beat from said absorber.

* * * * *